(12) United States Patent
Danilchik (10) Patent No.: US 8,408,044 B2
(45) Date of Patent: *Apr. 2, 2013

(54) AUTOMATED SYSTEMS AND METHODS FOR DETECTION OF CHEMICAL COMPOUNDS

(75) Inventor: Paul Danilchik, Poulsbo, WA (US)

(73) Assignee: Brooks Rand Inc, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,200

(22) Filed: Jun. 29, 2009

(65) Prior Publication Data

US 2009/0260421 A1    Oct. 22, 2009

Related U.S. Application Data

(63) Continuation of application No. 11/832,603, filed on Aug. 1, 2007, now Pat. No. 7,552,617.

(60) Provisional application No. 60/821,027, filed on Aug. 1, 2006.

(51) Int. Cl.
G01N 30/04 (2006.01)
B01D 53/02 (2006.01)
B01D 19/00 (2006.01)

(52) U.S. Cl. ............... 73/23.41; 73/19.12; 73/23.42; 95/87; 95/102; 95/156; 422/89

(58) Field of Classification Search .............. 73/19.12, 73/23.41, 23.42, 863.11, 863.12, 863.21, 73/863.23, 863.31, 863.32, 863.33; 95/87, 95/102, 156, 245; 422/101, 89, 500

See application file for complete search history.

(56) References Cited

U.S. PATENT DOCUMENTS

| | | | |
|---|---|---|---|
| 3,888,124 A * | 6/1975 | Campbell et al. | 73/863.21 |
| 4,023,929 A | 5/1977 | Becker et al. | |
| 4,399,032 A * | 8/1983 | Mott | 210/198.2 |
| 4,559,808 A * | 12/1985 | Sturman | 73/19.01 |
| 4,801,430 A * | 1/1989 | Robbat et al. | 422/52 |
| 5,012,845 A | 5/1991 | Averette | |
| 5,162,652 A * | 11/1992 | Cohen et al. | 250/288 |
| 5,229,300 A | 7/1993 | Yalvac et al. | |
| 5,551,278 A * | 9/1996 | Rounbehler et al. | 73/1.06 |
| 5,792,423 A * | 8/1998 | Markelov | 422/83 |
| 6,348,676 B2 * | 2/2002 | Kim et al. | 219/411 |
| 6,502,448 B1 | 1/2003 | Rapkin | |
| 6,511,852 B1 * | 1/2003 | Ledig | 436/181 |
| 6,541,272 B1 | 4/2003 | Mitra | |
| 6,667,467 B2 | 12/2003 | Shimizu et al. | |
| 6,920,802 B2 | 7/2005 | Newbound | |
| 7,028,562 B2 | 4/2006 | LaCourse et al. | |
| 7,303,727 B1 | 12/2007 | Dubrow et al. | |

(Continued)

OTHER PUBLICATIONS

Extended European Search Report dated Aug. 4, 2009, issued in corresponding European Patent Application No. 07811130.9, filed Aug. 2, 2007.

(Continued)

*Primary Examiner* — Daniel Larkin (74) *Attorney, Agent, or Firm* — Christensen O'Connor Johnson Kindness PLLC (57) ABSTRACT

Automated systems and methods for processing liquid test samples are generally provided. Automated systems generally include a gas and liquid separator configured for removing at least one volatile component from the test sample, a first trapping vessel in fluid communication with the gas and liquid separator, wherein the first trapping vessel contains a trapping material capable of adsorbing at least one of the at least one volatile component to provide at least one adsorbed component, and a heat source configured to heat the trapping material to a temperature sufficient to release at least one of the at least one adsorbed component from the trapping material to provide at least one released component.

25 Claims, 4 Drawing Sheets

U.S. PATENT DOCUMENTS

| | | |
|---|---|---|
| 7,713,742 B2 | 5/2010 | Schaedlich et al. |
| 2003/0086701 A1 | 5/2003 | Motz |
| 2003/0228699 A1 | 12/2003 | Shade et al. |
| 2004/0191126 A1 | 9/2004 | Heggs |

OTHER PUBLICATIONS

"Method 1630: Methyl Mercury in Water by Distillation, Aqueous Ethylation, Purge and Trap, and Cold Vapor Atomic Fluorescence Spectrometry," Draft Method, U.S. Environmental Protection Agency, Office of Water, Office of Science and Technology, Engineering and Analysis Division, Aug. 1998, 55 pages.

Second Office Action mailed Apr. 15, 2011, issued in corresponding Chinese Application No. 200780036562.X, filed Aug. 2, 2007, 13 pages.

* cited by examiner

AUTOMATED SYSTEMS AND METHODS FOR DETECTION OF CHEMICAL COMPOUNDS

CROSS-REFERENCES TO RELATED APPLICATIONS

This application is a continuation of U.S. application Ser. No. 11/832,603, filed Aug. 1, 2007, issued as U.S. Pat. No. 7,552,617 on Jun. 30, 2009, which claims the benefit of U.S. Provisional Application No. 60/821,027, filed Aug. 1, 2006, the disclosures of which are hereby expressly incorporated by reference.

FIELD OF THE INVENTION

The present invention provides methods and systems for the processing, detection and measurement of chemical compounds such as contaminants in samples such as water, soils, sediments, and biological materials.

BACKGROUND OF THE INVENTION

Mercury is a naturally occurring element that is known to have a toxic effect on human beings and animals in very low concentrations. Mercury's high toxicity combined with its penchant for bioaccumulation make it of particular concern among heavy metals. In particular, mercury can affect the nervous system, with fetuses, infants, and children being particularly sensitive to the effects of mercury. Methyl mercury is a highly toxic form of mercury found in sediments and water which is taken up by small organisms as they feed and subsequently accumulates in fish and shellfish that feed on such organisms. People and fish-eating wildlife, in turn, become exposed to methyl mercury when they ingest fish and shellfish containing methyl mercury. Detection and accurate measurement of methyl mercury in environmental and biological samples is thus of great interest. There are several ways of determining total mercury in environmental samples. However, speciation of mercury is more difficult.

Most methods currently employed in the analysis of methyl mercury levels are based on "Method 1630," entitled *Methyl Mercury in Water by Distillation, Aqueous Ethylation, Purge and Trap*, published by the U.S. Environmental Protection Agency. While this method is designed for monitoring water quality, it has been adapted for use with other types of samples by modifying the preparation steps. A sample is generally first subjected to either digestion, wherein the methyl mercury is leached from the sample; distillation, wherein the methyl mercury is carried from a distillation vessel and condensed in a receiving vessel, leaving many compounds other than water behind; or solvent extraction, with the resulting solvent containing the methyl mercury that is used for subsequent analysis.

The treated sample is then added to a vessel containing a larger volume of high purity de-ionized water, a buffer, and an ethylating reagent (generally sodium tetraethylborate). The ethylating reagent combines with various forms of mercury present in the sample resulting in formation of more complex "ethylated" molecules. The ethylated forms of mercury are fairly volatile and can therefore be stripped from the solution by bubbling a gas through the liquid. A gas, such as nitrogen, is utilized to purge the solution and carry the vapor to a tube that has been packed with a material that will retain a wide variety of substances and thus acts as a trap, retaining the ethylated forms of mercury. The trap packing material is designed such that the trapped molecules can be released by thermal desorption (i.e., heating the packing material and trapped molecules to the point where molecular vibrations overcome the attraction forces that keep the two together).

The trap is removed from the purge vessel and dried by allowing dry nitrogen gas to pass through it for a short time. After drying, the trap is manually connected to an inert gas source (generally argon or helium) and heated (for example using a nichrome wire coil) to release the ethylated species which are then carried out of the trap by the inert carrier gas flow to a gas chromatography (GC) column held at a fixed temperature. The different species, or forms, of mercury exit this column at different times based on their molecular mass, the temperature of the column and the gas-flow rate, with the smaller mercury species exiting the GC column before the larger species.

As the gas exits the GC column, it carries the different time-resolved mercury species into a quartz tube packed with quartz wool which is held at a very high temperature (referred to as a "pyrolytic" column) where, regardless of their molecular form, the mercury species are decomposed so that the atomic mercury is no longer bonded within a molecule. The resulting atomic mercury vapor is detected for each mercury species using, for example, a cold vapor atomic fluorescence spectrophotometer (CVAFS) such as that described in U.S. Pat. No. 5,731,873. The amount of each mercury species can then be quantified by comparison with results obtained for standard samples containing known levels of mercury.

This manual method for analyzing methyl mercury levels is time consuming and requires significant operator input. As with all manual techniques, there is significant inherent variability, with the method being prone to operator error. There thus remains a need in the art for systems and methods for the detection of low levels of contaminants, such as methyl mercury, which are both cost- and time-efficient, and require minimum operator input.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

An automated system that allows for efficient and cost-effective processing and/or detection of low levels of chemical compounds, or contaminants such as organomercury compounds, including, but not limited to, methyl mercury is provided, together with methods of using the automated system. The disclosed automated system is capable of processing, collecting, transferring, detecting, and analyzing low levels of chemical compounds in test samples. The automated system has several advantages over various manual chemical compounds processing and/or detection systems known in the art. For example, the automated system reduces the amount of operation labor, provides more procedural uniformity and better repeatability, and significantly increases the number of test samples that can be analyzed within a given period of time.

In one embodiment, the automated system for processing a liquid test sample comprises a gas and liquid separator, such as a purge vessel, an attachment for a gas source that provides a flow of gas for transferring the test sample from a sealable sample container to the gas and liquid separator and for removing volatile components from the test sample in the gas and liquid separator, wherein a chemical compound of interest present in the test sample is converted to a volatile species prior to transfer of the test sample into the gas and liquid separator, a trapping vessel in fluid communication with the gas and liquid separator, wherein the trapping vessel contains a material capable of separating the volatile species of the chemical compound from the volatile components and retaining the volatile species, and a heat source for rapidly heating the material in the trapping vessel to a temperature sufficient to release the volatile species from the material.

As used herein, volatile components, such as aldehydes, ketones, and hydrocarbons, are chemical compounds that have high enough vapor pressures under normal conditions to significantly vaporize and enter the atmosphere. Volatile compounds include, but are not limited to, methane; ethane; methylene chloride (dichloromethane); 1,1,1-trichloroethane (methyl chloroform); 1,1,2-trichloro-1,2,2-trifluoroethane (CFC-113); trichlorofluoromethane (CFC-11); dichlorodifluoromethane (CFC-12); chlorodifluoromethane (HCFC-22); trifluoromethane (HFC-23); 1,2-dichloro-1,1,2,2-tetrafluoroethane (CFC-114); chloropentafluoroethane (CFC-115); 1,1,1-trifluoro-2,2-dichloroethane (HCFC-123); 1,1,1,2-tetrafluoroethane (HFC-134a); 1,1-dichloro-1-fluoroethane (HCFC-141b); 1-chloro-1,1-difluoroethane (HCFC-142b); 2-chloro-1,1,1,2-tetrafluoroethane (HCFC-124); pentafluoroethane (HFC-125); 1,1,2,2-tetrafluoroethane (HFC-134); 1,1,1-trifluoroethane (HFC-143a); 1,1-difluoroethane (HFC-152a); parachlorobenzotrifluoride (PCBTF); cyclic, branched, or linear completely methylated siloxanes; acetone; perchloroethylene (tetrachloroethylene); 3,3-dichloro-1,1,1,2,2-pentafluoropropane (HCFC-225ca); 1,3-dichloro-1,1,2,2,3-pentafluoropropane (HCFC-225cb); 1,1,1,2,3,4,4,5,5,5-decafluoropentane (HFC 43-10mee); difluoromethane (HFC-32); ethylfluoride (HFC-161); 1,1,1,3,3,3-hexafluoropropane (HFC-236fa); 1,1,2,2,3-pentafluoropropane (HFC-245ca); 1,1,2,3,3-pentafluoropropane (HFC-245ea); 1,1,1,2,3-pentafluoropropane (HFC-245eb); 1,1,1,3,3-pentafluoropropane (HFC-245fa); 1,1,1,2,3,3-hexafluoropropane (HFC-236ea); 1,1,1,3,3-pentafluorobutane (HFC-365mfc); chlorofluoromethane (HCFC-31); 1-chloro-1-fluoroethane (HCFC-151a); 1,2-dichloro-1,1,2-trifluoroethane (HCFC-123a); 1,1,1,2,2,3,3,4,4-nonafluoro-4methoxy-butane (C4F9OCH3 or HFE-7100); 2-(difluoromethoxymethyl)-1,1,1,2,3,3,3-heptafluoropropane ((CF3)2CFCF2OCH3); 1-ethoxy-1,1,2,2,3,3,4,4,4-nonafluorobutane (C4F9OC2H5 or HFE-7200); 2-(ethoxydifluoromethyl)-1,1,1,2,3,3,3-heptafluoropropane ((CF3)2CFCF2OC2H5); methyl acetate; 1,1,1,2,2,3,3-heptafluoro-3-methoxy-propane (n-C3F7OCH3 or HFE-7000); 3-ethoxy-1,1,1,2,3,4,4,5,5,6,6,6-dodecafluoro-2-(trifluoromethyl)hexane (HFE-7500); 1,1,1,2,3,3,3-heptafluoropropane (HFC-227ea); methyl formate (HCOOCH3); and other perfluorocarbon compounds.

In other embodiments, the automated system may additionally comprise a holder for carrying a plurality of sample containers, a gas chromatography (GC) system, and a pyrolytic column. The sample containers, the gas and liquid separator, the trapping vessel, the GC system, the pyrolytic column, and other components of the automated system are in fluid communication with one another by way of a plurality of tubular members. As used herein, the term "fluid communication" connotes liquid communication and/or gaseous communication.

In one embodiment, a chemical compound of interest present in a test sample is converted to at least one volatile species prior to transfer of the test sample into the gas and liquid separator or purge vessel. The volatile species are removed from the test sample in the purge vessel, and then absorbed by trapping material within the trapping vessel. The volatile species are subsequently and rapidly released from the trapping material by means of ballistic heating. The volatile species may subsequently be separated by the GC system, which may be operated at around room temperature. The separated volatile species are next heated in a pyrolytic column to form elemental form(s) of the compound, which are then measured by a detection device.

In another embodiment, mercury species within a test sample are either ethylated to give volatile ethylated mercury species, or propylated to give volatile propylated mercury species, which are removed from the sample in the purge vessel, and then absorbed by trapping material within the trapping vessel. The ethylated or propylated mercury species are: subsequently and rapidly released from the trapping material by means of ballistic heating and separated by the GC system, which may be operated at around room temperature. The separated ethylated or propylated mercury species are heated in a pyrolytic column to form elemental mercury which is then measured by a detection device.

The sample container may be, but is not limited to, a sealable autosampler vial. In one embodiment, to prepare a test solution, a mixture of a test sample, water, such as high purity de-ionized water, a buffer, such as an acetate buffer, is added to the sample container. The sample container is filled to the top to ensure that no air bubbles remain and is then sealed. In another embodiment, to prepare a test solution, a mixture of a test sample, water, such as high purity de-ionized water, a buffer, such as an acetate buffer, and an ethylating reagent, such as sodium tetraethylborate, is added to the sample container. The ethylating reagent reacts with any mercury present in the test solution, resulting in the formation of volatile ethylated mercury species in the container. Alternatively, a propylating agent may be employed to form volatile propylated mercury species. The sample container is filled to the top to ensure that no air bubbles remain and is then sealed.

The automated system may further comprise a piercing needle assembly. A needle of the piercing needle assembly pierces and enters the sample container. The gas source, for example, nitrogen, is passed into the sample container via the piercing needle assembly's ventilation port and the resulting gas pressure forces the test solution from the sample container into the gas and liquid separator via a switchable valve connected to the bottom of the gas and liquid separator.

In one embodiment, the gas and liquid separator is a purge vessel. The purge vessel may be an elongated tube comprising at least two ports, with the first port being positioned at the top of the purge vessel and the second port being positioned at the bottom of the purge vessel. The test solution enters the purge vessel via the second port and fills the purge vessel. The gas source is next introduced into the purge vessel, causing bubbles to travel up and through the test solution, and stripping it of the volatile species which exit the purge vessel via the first port. The gas source may be a continuation of the flow of gas that provided the pressure to force the test solution from the sample container into the gas and liquid separator.

The volatile species are next passed through a valve system towards the trapping vessel, which is capable of collecting (adsorbing), drying, and thermally desorbing the volatile species. The trapping vessel, which may be constructed of Pyrex® glass or quartz, contains at least one type of trapping material for collecting, adsorbing, or trapping the volatile species.

It will be appreciated that the above-described "purge and trap" system, comprising at least one gas and liquid separator for separating volatile species from a test sample and at least one trapping vessel in fluid communication with the gas and liquid separator for trapping the volatile species, is not limited for use with volatile species, and that the "purge and trap" system may be used for separating and trapping other chemical compounds and/or contaminants.

After the volatile species are adsorbed or trapped by the packing material, the trapping vessel is dried by way of the gas source, which travels through the valve system into the trapping vessel. The trapping vessel is heated by a heat source, and may optionally be in communication with a cooling system.

In one embodiment, the heat source comprises at least one halogen bulb capable of providing infra-red emissions. The infra-red emissions provided by the halogen bulb rapidly and intensely heat the trapping material in the trapping vessel. This method of rapid and intense heating of the trapping material may be referred to as "ballistic heating." The accumulated thermal energy generated by the ballistic heating within the trapping vessel results in the rapid release of the volatile species from the trapping material by way of thermal desorption.

The automated system may further comprise an inert gas carrier source. The inert gas carrier may be, but is not limited to, argon, helium, neon, krypton, xenon, or radon. The inert gas carrier enters the trapping vessel by way of another valve system. The volatile species released from the trapping material in the trapping vessel is mixed with the inert gas carrier, and the resulting mixture exits the trapping vessel and passes through the valve system towards a junction, from where the mixture of the volatile species and the inert gas carrier may travel to the gas chromatographic (GC) system.

The GC system comprises a GC column containing at least one GC packing material, such as OV-3 on Chromasorb W, held at a fixed temperature, and a pyrolytic column. The GC system is in gaseous communication with a detection device, such as a spectrophotometer. The GC column can be in any configuration. In one embodiment, the GC column is S-shaped and constructed of Teflon® tubing, while having a total length of about nine inches and operates at a relatively low temperature (about 35° C.). In another embodiment, the GC column is U-shaped and constructed of Teflon® tubing, while having a total length of about nine inches and operates at a relatively low temperature (about 35° C.). Different forms of the ethylated or propylated mercury species exit the GC column at different times, depending on their molecular size.

In one embodiment, after passage through the GC column, the various forms of volatile species are passed through a pyrolytic column. The pyrolytic column, by way of extreme heat, is capable of breaking down and converting the various forms of volatile species into elemental form(s) of the test compound. The pyrolytic column is heated by means of a heat source, such as a coil of nichrome wire. Electrical potential is provided across the nichrome wire coil, which induces an electrical current to flow through the wire coil. Resistive losses of the nichrome wire cause the pyrolytic column to become intensely hot, resulting in the steady heating of the pyrolytic column, and the accumulated thermal energy within the pyrolytic column induces chemical breakdown of the various volatile species into elemental form(s) of the test compound.

Molecules of elemental form(s) of the test compound that exit from the pyrolytic column may be passed into a detection device, such as a spectrophotometer, where the amount of elemental form(s) of the test compound exiting the GC column at specific times is measured. The spectrophotometer may be, for example, a cold vapor atomic fluorescence spectrophotometer (CVAFS).

In another embodiment, the automated system comprises a holder for carrying a plurality of sample containers, a purge vessel, at least three trapping vessels, and a gas chromatography (GC) system. Each of the trapping vessels is connected to a heat source, such as a halogen bulb, and is capable of performing the collection (adsorption), drying, and thermal desorption of volatile species. This system allows the simultaneous operation of a first trapping vessel adsorbing volatile species, while a second trapping vessel is being dried, and volatile species in a third trapping vessel are being thermally desorbed.

In this embodiment, a first sample of volatile species exits the purge vessel and is passed through a first valve system towards a first trapping vessel via a first three-port valve. After the first sample of the volatile species is adsorbed or trapped by the packing material in the first trapping vessel, the first trapping vessel is dried by way of the gas source, and the volatile species are then released by thermal desorption as described above.

As the first sample of volatile species trapped in the first trapping vessel is being dried, a second sample of volatile species exits from the purge vessel and enters the second trapping vessel via a second three-port valve. Once the second sample of volatile species is adsorbed or trapped by the packing material in the second trapping vessel, the second trapping vessel is dried by way of the gas source, which travels through the three-port into the second trapping vessel, and the volatile species are released by way of thermal desorption.

As the second sample of the volatile species trapped in the second trapping vessel is being dried, a third sample of volatile species exits from the purge vessel and enters the third trapping vessel via a third three-port valve. After the third sample of the volatile species is adsorbed or trapped by the packing material in the third trapping vessel, the third trapping vessel is dried by way of the gas source, which travels through the third two-port valve into the third trapping vessel, and the volatile species are released by way of thermal desorption. The automated cycle described above involving the first, second, and third trapping vessels repeats continuously.

In alternative embodiments, the automated system comprises one, two, four, or more trapping vessels.

Methods for determining the amount of chemical compounds present in a test sample are also provided. In certain embodiments, such methods comprise: placing liquid test sample(s) in sealable container(s), transferring the liquid test sample(s) from the sealable container(s) to at least one gas and liquid separator using a flow of a gas, separating the volatile species of the chemical compounds from the test sample(s), absorbing the volatile species onto trapping material(s), and rapidly heating the trapping material(s) to a temperature sufficient to release the volatile species. In other embodiments, the volatile species may be separated by means of gas chromatography, and each of the separated volatile species may be heated to a temperature sufficient to form elemental form(s) of the test compound, and the amount of each elemental form of the test compound formed from each of the separated volatile species may be determined.

The use of multiple trapping vessels and the plurality of valve systems in the automated system disclosed herein provides the advantage of simultaneous adsorption, drying, and thermal desorption of multiple samples of volatile species, with the need for only one purge vessel and one GC system, thereby significantly enhancing the efficiency and output of the system. In addition, thermal desorption in chemical compound processing and detection systems known in the art is generally accomplished by placing the trapping vessel within a coil of nichrome wire, and providing electrical potential across the coil to provide passage of electrical current. This results in resistive heating of the coil windings around the trapping vessel, which initially heats only the outer layer of the trapping material. Although the entire content of the trapping material is eventually heated, the heating of the trapping material is neither rapid nor uniform. In contrast, the use of ballistic heating in the disclosed automated system significantly reduces the time necessary for heating and provides uniform heating of the trapping material, thereby reducing the amount of time required for thermal desorption of the volatile species.

The GC column employed in the disclosed automated system is significantly shorter than GC columns generally employed in the art, thereby allowing the GC column to be operated at around 35° C., instead of 90° C. to 150° C. as required by the GC columns generally employed in the art. This provides the advantages of reduced space and materials requirements and reduced power consumption, leading to significant cost savings.

Further, chemical compound processing and detection systems known in the art generally utilize peristaltic pump systems to transfer a test sample from a sample container to the purge vessel. However, volatile species tend to adhere to the flexible tubing required in such systems. In one example, while methyl mercury does not adhere to fluoropolymer tubing, such as Teflon® tubing, such tubing is not suitable for use with a peristaltic pump due to its rigidity. As the disclosed automated system employs a gas source instead of a peristaltic pump system to transfer the test sample from the sample container to the purge vessel, Teflon® tubing may be employed in the disclosed system.

In accordance with another embodiment of the present disclosure, an automated system for processing a liquid test sample is provided. The system generally includes a gas and liquid separator configured for removing at least one volatile component from the test sample. The system further includes a first trapping vessel in fluid communication with the gas and liquid separator, wherein the first trapping vessel contains a trapping material capable of adsorbing at least one of the at least one volatile component to provide at least one adsorbed component. The system further includes an infrared heat source configured to heat the trapping material to a temperature sufficient to release at least one of the at least one adsorbed component from the trapping material to provide at least one released component.

In accordance with another embodiment of the present disclosure, an automated system for processing a liquid test sample is provided. The system generally includes a gas and liquid separator configured for removing at least one volatile component from the test sample. The system further includes at least two trapping vessels in fluid communication with the gas and liquid separator, wherein the at least two trapping vessels contain a trapping material capable of adsorbing at least one of the at least one volatile component to provide at least one adsorbed component. The system further includes a heat source configured to heat the trapping material to a temperature sufficient to release at least one of the at least one adsorbed component from the trapping material to provide at least one released component.

In accordance with another embodiment of the present disclosure, an automated system for processing a liquid test sample is provided. The system generally includes a first conduit for providing a flow of gas to a test sample container, and a gas and liquid separator in fluid communication with the first conduit, the gas and liquid separator configured for removing at least one volatile component from the test sample. The system further includes a trapping vessel in fluid communication with the gas and liquid separator, wherein the first trapping vessel contains a trapping material capable of adsorbing at least one of the at least one volatile component to provide at least one adsorbed component. The system further includes a heat source configured to heat the trapping material to a temperature sufficient to release at least one of the at least one adsorbed component from the trapping material to provide at least one released component.

In accordance with another embodiment of the present disclosure, an automated system for processing a liquid test sample is provided. The system generally includes a gas and liquid separator, and an attachment for a first gas source that provides a flow of gas for transferring a test sample to the gas and liquid separator and for removing at least one volatile component from the test sample in the gas and liquid separator, wherein an organomercury compound present in the test sample is converted to at least one ethylated or propylated mercury species prior to transfer of the test sample into the gas and liquid separator. The system further includes a trapping vessel in fluid communication with the gas and liquid separator, wherein the trapping vessel contains at least one material capable of adsorbing the at least one ethylated or propylated mercury species of the organomercury compound. The system further includes a heat source for heating the at least one material in the trapping vessel to a temperature sufficient to release the at least one ethylated or propylated mercury species from the at least one material.

In accordance with another embodiment of the present disclosure, a method processing a liquid test sample is provided. The method generally includes placing a liquid test sample in a sealable container, transferring the sample from the container to a gas and liquid separator using a first flow of gas, and separating at least one volatile component from the sample in the gas and liquid separator. The method further includes adsorbing at least one of the at least one volatile component onto a trapping material to provide at least one adsorbed component, and releasing at least one of the at least one adsorbed component from the trapping material to provide at least one released component.

In accordance with another embodiment of the present disclosure, a method processing a liquid test sample is provided. The method generally includes placing a liquid test sample in a sealable container, transferring the sample from the container to a gas and liquid separator, and separating at least one volatile component from the sample in the gas and liquid separator. The method further includes adsorbing at least one of the at least one volative component onto a trapping material to provide at least one adsorbed component, and heating the trapping material using infrared heat to a temperature sufficient to release at least one of the at least one adsorbed component from the trapping material to provide at least one released component.

In accordance with another embodiment of the present disclosure, a method processing a liquid test sample is provided. The method generally includes placing a liquid test sample in a sealable container, transferring the sample from the container to a gas and liquid separator, and separating at least one volatile component from the sample in the gas and liquid separator. The method further includes adsorbing at least one of the at least one volative component onto a trapping material in one of at least two trapping vessels in fluid communication with the gas and liquid separator to provide at least one adsorbed component, and releasing at least one of the at least one adsorbed component from the trapping material to provide at least one released component.

These and additional features of the present invention and the manner of obtaining them will become apparent, and the invention will be best understood, by reference to the following more detailed description and the accompanying drawings.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

The present invention will be described in greater detail in the following detailed description, with reference to the accompanying drawings, wherein.

DETAILED DESCRIPTION OF THE INVENTION

Figure 1A:
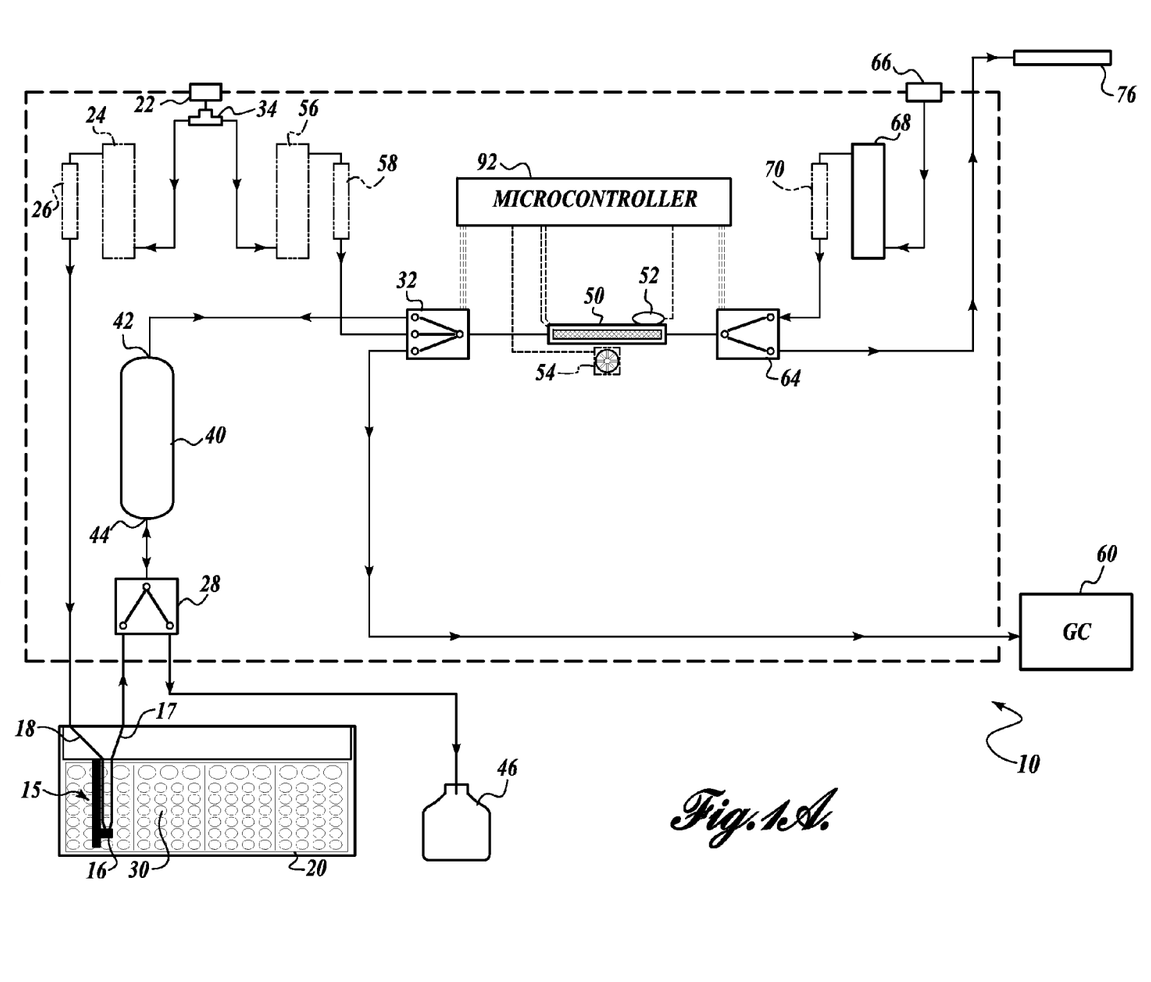
FIG. 1A shows an embodiment of an automated system for chemical compound processing and detection.

FIG. 1A shows an embodiment of the disclosed automated system 10 for processing and/or detecting low levels of organomercury compounds, including, but not limited to, methyl mercury. In the embodiment, shown in FIG. 1A, automated system 10 comprises a holder 20 for carrying a plurality of sample containers 30, a gas and liquid separator, or purge vessel 40, a trapping vessel 50, and a gas chromatography (GC) system 60. The sample containers 30, purge vessel 40, trapping vessel 50, gas chromatography (GC) system 60, and other components of the automated system 10 are in fluid communication with one another by way of a plurality of tubular members. As used herein, the term "fluid communication" refers to liquid communication and/or gaseous communication. Tubular members may be formed from, but are not limited to, a fluoropolymer, such as Teflon® tubing.

Figure 1B:
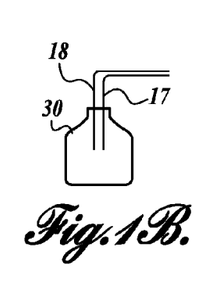
FIG. 1B shows a close up of a sample container in the automated system of FIG. 1A.

Sample container 30 may be, but is not limited to, a sealable autosampler vial. In this embodiment, to prepare a test solution, a mixture of a test sample, water, such as high purity de-ionized water, a buffer, such as an acetate buffer, and an ethylating reagent, such as sodium tetraethylborate, is added to sample container 30. The test sample may be, but is not limited to, a liquid believed to contain mercury, a mercury standard, or a blank such as water. The ethylating reagent reacts with any mercury present in the test solution, resulting in the formation of ethylated mercury species in container 30. Alternatively, a propylating reagent may be used in place of the ethylating agent to provide propylated mercury species. Sample container 30 is filled to the top to ensure that no air bubbles remain and then sealed. As sample container 30 contains a minimal amount of air, the ethylated or propylated mercury species are capable of remaining stable for many hours before the test solution is transferred to automated system 10 and analyzed. A close-up view of a sample container 30 can be seen in FIG. 1B.

Automated system 10 further comprises a piercing needle assembly 15. A needle 16 of the piercing needle assembly 15 pierces and enters sample container 30. A vent line 18 becomes pressurized by way of gas source 22, which in turn pressurizes container 30 during and after the needle piercing operation. The filling operation takes place by way of a portal in the tip of needle 16, which allows the test sample to flow out through tip line 16 to and through valve 28 and into the bottom of purge vessel 40 via port 44. Once the filling operation is complete, the gas continues to flow and strips any residual from the inside of container 30, tip line 16, valve 28, and the tubing leading to purge vessel 40. The gas also facilitates stripping of the volatile species from the test sample solution into the gas stream, which exits via port 42 toward valve system 32 and trapping vessel 50.

In one embodiment, a gas, for example, nitrogen, is passed from gas source 22 through junction 34 into sample container 30 via a ventilation port of the piercing needle assembly 15. Before the gas from gas source 22 reaches sample container 30, it may optionally pass through at least one flow control device 24 for measuring and/or controlling the flow rate of the gas. Flow control device 24 may be, but is not limited to, a mass flow controller or a rotameter. Gas from gas source 22 may also optionally pass through at least one purifying device 26 to eliminate any mercury that may be present in the gas. Purifying device 26 may be, but is not limited to, a gold cleanup column. The resulting gas pressure in sample container 30 forces the test solution from the container into purge vessel 40 via a switchable valve 28, such as an A/B valve, positioned near the bottom of purge vessel 40. After the entire test solution is transferred from sample container 30 into purge vessel 40, the gas flow is continued in order to strip the inside walls of sample container 30 of any residual materials. The gas flow also strips any volatile species from small droplets or film that might remain in the transfer tubing.

In the embodiment shown in FIG. 1A, purge vessel 40 is an elongated tube comprising at least two ports 42 and 44, although other configurations may also be utilized with automated system 10. The first port 42 is positioned at the top of purge vessel 40 with the second port 44 being positioned at the bottom of purge vessel 40. The test solution enters purge vessel 40 via port 44 and at least partially fills the purge vessel 40. Gas from gas source 22 is next introduced into purge vessel 40 at or near the bottom of purge vessel 40, which causes bubbles to travel up and through the test solution and strips it of the volatile ethylated or propylated mercury species which exit purge vessel 40 via port 42. After substantially all the ethylated or propylated mercury species have been removed from the test solution, switchable valve 28 is switched and the gas flow is reversed such that the gas from gas source 22 enters purge vessel 40 from the top, resulting in the rapid draining of the test solution into a waste receptacle 46 via port 44. The gas flow continues after substantially all of the test solution is removed from purge vessel 40, in order to strip the vessel of any residual material that may otherwise remain and possibly contaminate subsequent operations of automated system 10.

The ethylated or propylated mercury species that exit purge vessel 40 next pass through valve system 32 and enter trapping vessel 50. Valve system 32 may be, but is not limited to, an AB valve, a three-port valve, a two-port valve, and the like. Trapping vessel 50 is capable of performing the collection (adsorption), drying, and thermal desorption of the ethylated mercury or propylated species, and may be constructed of Pyrex® glass, quartz, or other suitable materials. Trapping vessel 50, which contains at least one trapping material for collecting, adsorbing, or trapping the ethylated or propylated species, is connected to a heat source 52, and optionally a cooling system 54, such as a cooling fan. Any trapping material known in the art that is capable of efficiently trapping the ethylated or propylated mercury species, such as graphitized carbon or Tenax™, may be employed in trapping vessel 50.

After the ethylated or propylated mercury species are adsorbed or trapped by the packing material, trapping vessel 50 is dried by way of a gas, such as nitrogen. As shown in FIG. 1A, the gas passes from gas source 22, through juncture device 34, through an optional flow control device 56, such as a mass flow controller or a rotameter, an optional purifying device 58, and valve system 32 into trapping vessel 50.

Heat source 52 which may be, for example, a halogen bulb, is capable of providing infra-red emissions. The infra-red emissions provided by heat source 52 rapidly and intensely heat the trapping material in trapping vessel 50. The heating by heat source 52 preferably takes less than about twenty seconds. For example, heat source 52 may be employed to heat trapping vessel 50 for about eight to twenty seconds, about eight to twelve seconds, about twelve to sixteen seconds, or about sixteen to twenty seconds. In one embodiment, the heating by heat source 52 lasts about eight seconds, and is sufficient to cause the temperature of the trapping material in trapping vessel 50 to increase to about 200° C. The accumulated thermal energy within the trapping vessel 50 results in the rapid release of the ethylated or propylated mercury species from the trapping material by way of thermal desorption, wherein the molecular vibrations caused by the heat overcomes the attraction forces between the ethylated or propylated mercury species and the trapping material.

Automated system 10 further comprises an inert gas carrier source 66. The inert gas carrier may be, but is not limited to, argon, helium, neon, krypton, xenon, or radon. In one embodiment, the inert gas carrier is argon. The inert gas carrier from source 66 passes through a flow control device 68 and an optional purifying device 70, and enters trapping vessel 50 by way of a valve system 64. Flow control device 68 may be, but is not limited to, a mass flow controller or a rotameter. The ethylated or propylated mercury species released from the trapping material in trapping vessel 50 are mixed with the inert gas carrier, and the resulting mixture exits the trapping vessel 50 and passes through valve system 32 towards GC system 60. The drying or purging gas, such as nitrogen, may exit the system via valve system 64 and enter exhaust trap 76.

As shown in FIG. 1A, valve systems 32 and 64, heat source 52, and cooling device 54 are in electronic communication with a microcontroller 92, which can be connected to any computer system suitable for the control and automation of automated system 10. Such computer systems are well known in the art.

Figure 2:
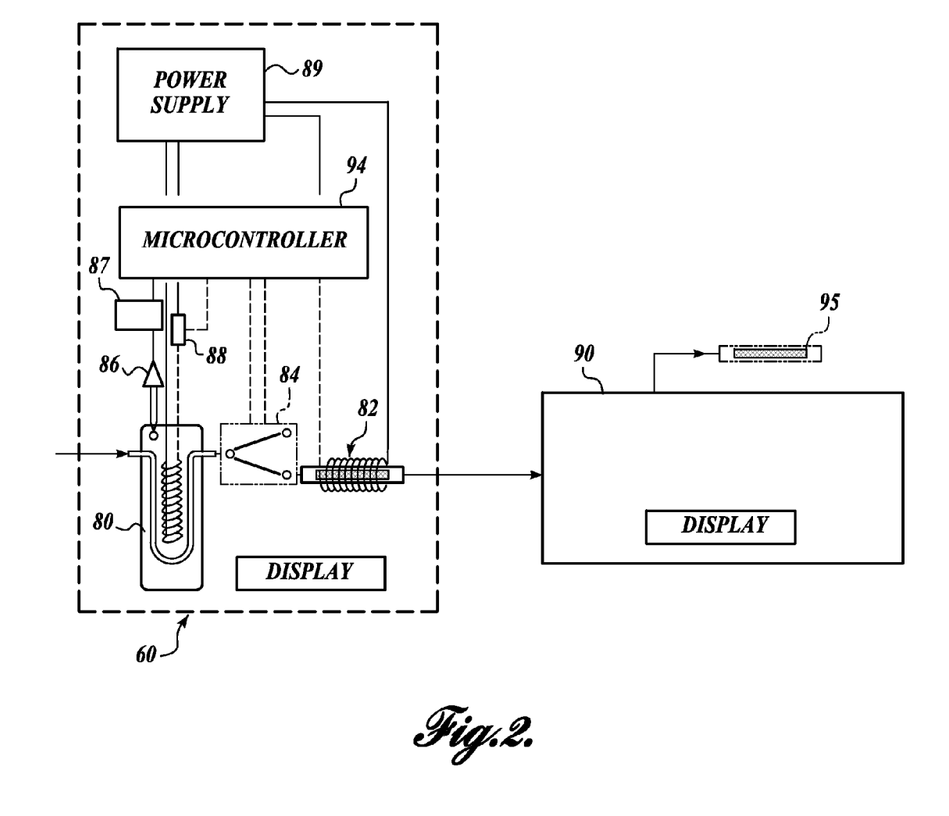
FIG. 2 shows an embodiment of a gas chromatography (GC) system of the automated system of FIG. 1A.

After being released from trapping vessel 50, the mixture of the ethylated or propylated mercury species and the inert gas carrier travels to gas chromatographic (GC) system 60. As shown in FIG. 2, GC system 60 comprises a GC column 80 containing a GC packing material, such as OV-3. GC column 80 may be held at a fixed temperature, and therefore the GC column 80 in the illustrated embodiment includes a temperature sensor 86, a temperature control 87, a heat control 88, and a power supply 89. Molecules of the released ethylated or propylated mercury species travel from the entrance to the exit of GC column 80 at a speed that is determined by the mass of the molecules. Larger molecules, having a higher attraction to the GC packing material, are bonded to the GC packing material for a longer period, and are thereby released from the GC column 80 more slowly than smaller molecules of ethylated or propylated mercury species. In general, $Hg^0$ first exits the GC column 80, followed by methyl mercury, and then $Hg^{2+}$. Since the rate that the mercury molecules travel is also dependent on the temperature of the GC packing material and gas flow rate, those variables are optimized and then typically held constant. Generally, each form of ethylated or propylated mercury species exits GC column 80 such that they do not overlap each other.

While the total length of GC column 80 may be varied, GC column 80 generally has a shorter total length than that of conventional GC columns known in the art. GC column 80 may measure between about two inches and about thirty-six inches, between about two inches and about nine inches, between about ten inches and about twenty inches, or between about twenty-one inches and about thirty-six inches. In one embodiment, the total length of GC column 80 is about nine inches. GC column 80 can be operated at a relatively low temperature, for example, at about 35° C. The GC column 80 is preferably constructed from a non-reactive material, such as Teflon®. Heat is provided to GC column 80 by way of a heating source, such as an aluminum heating block (not shown). In one embodiment, the aluminum heating block measures about four inches, by two inches, by one inch.

The different ethylated or propylated mercury species exit the GC column 80 and are transferred to a pyrolytic column 82 by way of an optional valve system 84. The pyrolytic column 82 is capable of breaking down and converting the various forms of the ethylated or propylated mercury species into the elemental form of mercury. Pyrolytic column 82 is heated by means of a heat source 85, such as a nichrome wire coil, that heats pyrolytic column 82 to a temperature of about 700° C., although any temperature sufficient to decompose the ethylated or propylated mercury species can be employed. Heat may be supplied, for example, by a bulk heat source and an electrical current applied to the nichrome wire coil.

The elemental mercury molecules next exit the pyrolytic column 82 and are passed into a spectrophotometer 90 where the elemental mercury molecules are detected and measured. Spectrophotometers 90 suitable for use with GC system 60 include, but are not limited to, a cold vapor atomic fluorescence spectrophotometer (CVAFS) as described in U.S. Pat. No. 5,731,873. Spectrophotometer 90 may optionally be connected to a pollution control device 95, such as an iodated carbon column. As shown in FIG. 2, the GC system 60 is in electronic communication with a microcontroller 94, which can be connected to any computer system for the control and automation of GC system 60. In one embodiment of automated system 10, one microcontroller, such as the microcontroller 92 as shown in FIG. 1A, may be employed to control the entire automated system 10.

A mercury vapor light source having a strong emission of 254 nm UV light excites any mercury atoms passing through the detection cell of the spectrophotometer 90. The excited mercury atoms re-emit the same wavelength light when they spontaneously return to their ground state. This fluorescence emission can be detected at a right angle to the incident light source such that the detected fluorescence is maximized and the detected incident beam and its scatter are minimized. The detected signal coming from a photomultiplier detector and the 254 nm optical filter is amplified and then measured. A continuous measurement is made of this signal, which is used to quantify the relative measure of atomic mercury passing through the cell at any given moment. This type of system is quite linear and provides precise relative measurement of the mercury density in the inert carrier gas over more than four orders of magnitude (>10,000:1 range). Since the amount of atomic mercury is proportional to amount of the ethylated or propylated mercury species exiting the GC system 60, it is possible to compare the results obtained from test samples with those obtained using "standard" samples having known levels of methyl mercury, allowing samples having an unknown concentration of a specific mercury species to be quantified with a known level of certainty.

Figure 3:
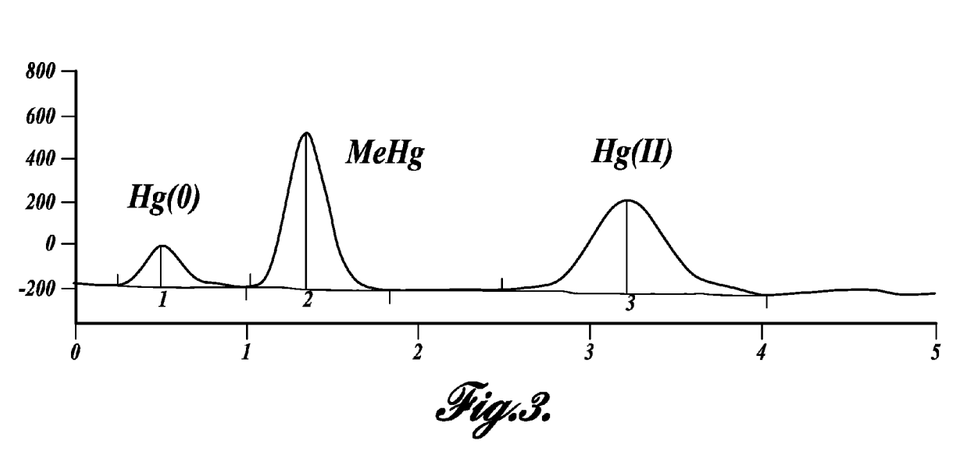
FIG. 3 shows an exemplary gas chromatography peak analysis graph, produced by the disclosed automated system.
Figure 4:
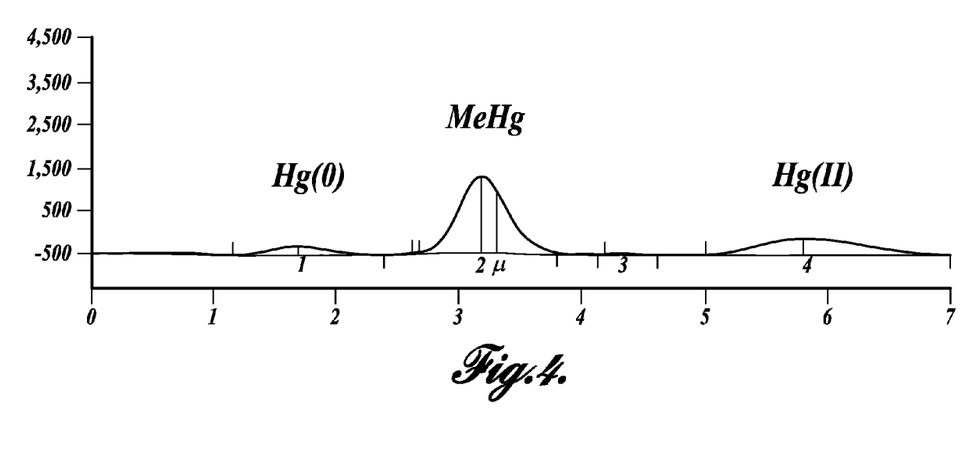
FIG. 4 shows an exemplary gas chromatography peak analysis graph, produced by a conventional methyl mercury detection system.

As shown in FIGS. 3 and 4, use of a system disclosed herein, including ballistic heating of the trapping vessel, with a GC column approximately nine inches in length, operating at a low temperature of about 35° C., resulted in a much shorter duration run time than that obtained using a conventional methyl mercury detection system. Specifically, the entire chromatographic process could be accomplished in under about five minutes using the automated system disclosed herein (FIG. 3), compared to a run time of about seven to eight minutes using the conventional methyl mercury detection system (FIG. 4).

Figure 5:
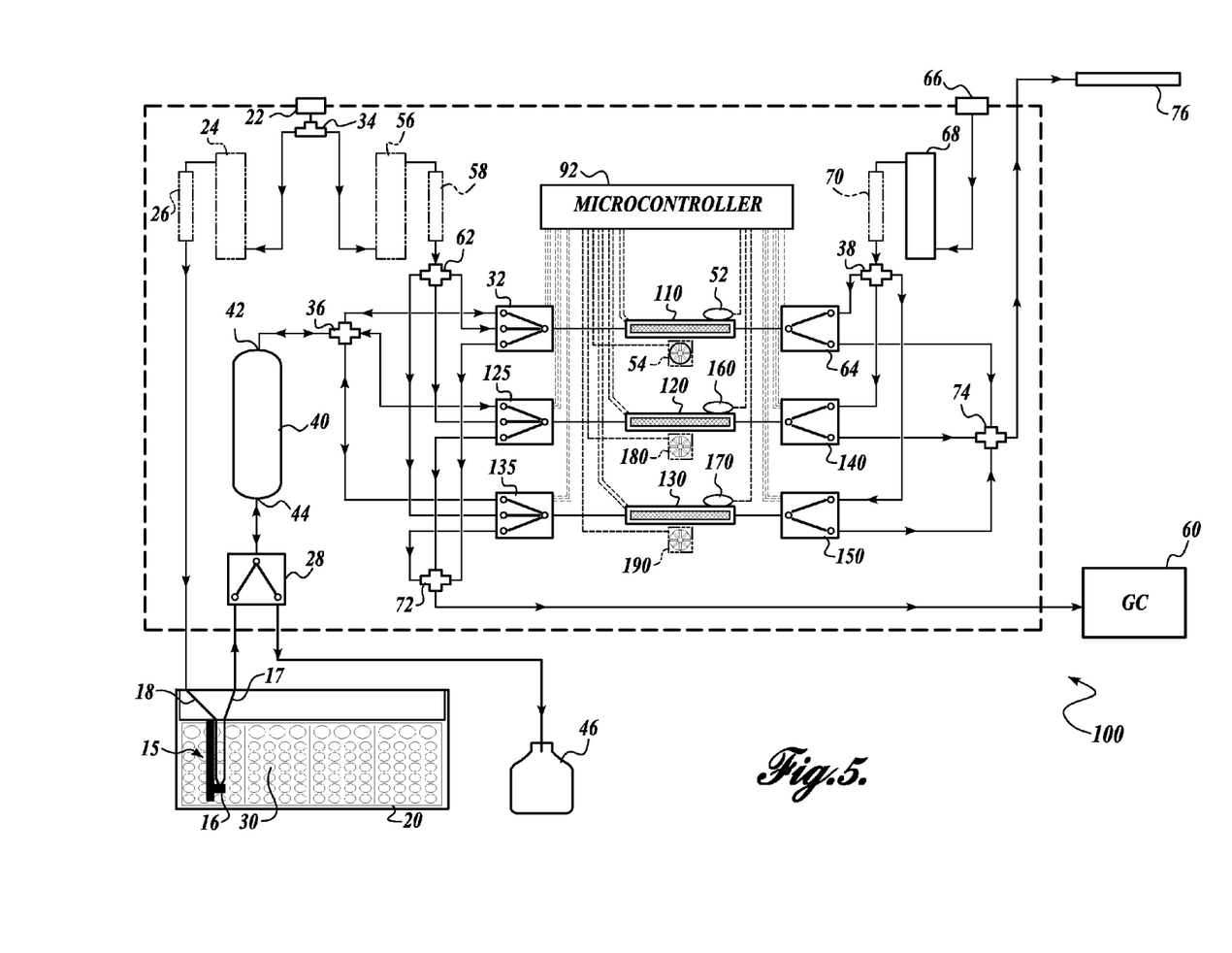
FIG. 5 shows another embodiment of an automated system for chemical compound processing and detection.

FIG. 5 shows another embodiment of the automated system 100 for collecting, transferring, detecting, and analyzing low levels of methyl mercury. Automated system 100 comprises a holder 20 for carrying a plurality of sample containers 30, a purge vessel 40, at least three trapping vessels 110, 120 and 130, and a gas chromatography (GC) system 60 (shown in FIG. 2). With the exception of the three trapping vessels 110, 120 and 130, it will be appreciated that all the system components of automated system 100 shown in FIG. 5, are the same as the system components of automated system 10, shown in FIG. 1A. Automated system 100 further comprises three three-port valves 32, 125 and 135; and three two-port valves 64, 140 and 150. Automated system 100 allows the simultaneous operation of a first trapping vessel adsorbing ethylated or propylated mercury species, while a second trapping vessel is being dried and ethylated or propylated mercury species in a third trapping vessel are being thermally desorbed.

Trapping vessels 110, 120 and 130 each comprise at least one trapping material for collecting, adsorbing, or trapping the ethylated or propylated mercury species. Each of trapping vessels 110, 120, and 130 are capable of performing the collection (adsorption), drying, and thermal desorption of the ethylated or propylated mercury species, and are heated by heat sources 52, 160 and 170, respectively. Heat sources 52, 160 and 170, which are preferably halogen bulbs, are capable of ballistically heating trapping vessels 110, 120 and 130, respectively. Trapping vessels 110, 120 and 130 may also be connected to cooling systems 54, 180 and 190, such as cooling fans.

In the embodiment shown in FIG. 5, after the ethylated or propylated mercury species from a first test solution exits purge vessel 40 via port 42, they pass through junction 36 and a first valve system 32 to first trapping vessel 110. After the first sample of ethylated or propylated mercury species is adsorbed or trapped by the packing material in first trapping vessel 110, first trapping vessel 110 is dried by way of a gas, such as nitrogen, from gas source 22. As with the embodiment shown in FIG. 1A, the nitrogen gas passes through a flow control device 56 and an optional purifying device 58, and towards a junction device 62, wherein the gas source 22 travels through first valve system 32 into first trapping vessel 110. In this embodiment, a first heat source 52, such as a halogen bulb, causes the rapid release of the ethylated or propylated mercury species from the trapping material in trapping vessel 110 by way of thermal desorption. The released ethylated or propylated mercury species are mixed with an inert gas carrier from source 66, which passes through junction 38 and enters the first trapping vessel 110 via two-port valve 64. The resulting mixture exits first trapping vessel 110, passes through valve system 32 towards junction 72, and then travels to gas chromatographic (GC) system 60, as shown in FIG. 1A and described above, for the subsequent detection and analysis of methyl mercury. The drying or purging gas, such as nitrogen, may exit the system via valve system 64, then pass through junction 74 to enter exhaust trap 76.

As the sample of ethylated or propylated mercury species trapped in the first trapping vessel 110 is being dried, a second sample of ethylated or propylated mercury species exits from purge vessel 40, passes through junction 36 and enters a second trapping vessel 120 via three-port valve 125. After the second sample of the ethylated or propylated mercury species is adsorbed or trapped in second trapping vessel 120, second trapping vessel 120 is dried by way of a gas from gas source 22, which travels through the second valve system 125 into the second trapping vessel 120. The infra-red emissions provided by the second heat source 160 heat the trapping material in the second trapping vessel 120, resulting in the release of the second sample of ethylated or propylated mercury species by way of thermal desorption. The ethylated or propylated mercury species released from the trapping material in the second trapping vessel 120 are mixed with inert gas carrier from source 66, which passes through junction 38 and enters the second trapping vessel 120 via two-port valve 140. The resulting mixture exits second trapping vessel 120, passes through valve system 125 to junction 72 and then travels to gas chromatographic (GC) system 60. The drying or purging gas, such as nitrogen, may exit the system via valve system 64, then pass through junction 74 to enter exhaust trap 76.

As the ethylated or propylated mercury species trapped in the second trapping vessel 120 are being dried, a third sample of ethylated or propylated mercury species exits from purge vessel 40, passes through junction 36 and enters a third trapping vessel 130 via three-port valve 135. After the third sample of the ethylated or propylated mercury species is adsorbed or trapped by the packing material in third trapping vessel 130, third trapping vessel 130 is dried by way of gas from source 22, which travels through the third valve system 135 into the third trapping vessel 130. The infra-red emissions provided by the third heat source 170 heat the trapping material in the third trapping vessel 130, thereby releasing the third sample of ethylated or propylated mercury species by way of thermal desorption. The ethylated or propylated mercury species released from the trapping material in the third trapping vessel 130 are mixed with inert gas carrier from source 66, which passes through junction 38 and enters the third trapping vessel 130 via two-port valve 150. The resulting mixture exits third trapping vessel 130, passes through valve system 135 to junction 72, and travels to gas chromatographic (GC) system 60. The drying or purging gas, such as nitrogen, may exit the system via valve system 64, then pass through junction 74 to enter exhaust trap 76.

The automated cycle described above involving the first, second, and third trapping vessels 110, 120 and 130 may be repeated continuously. In one exemplary operation of automated system 100, the adsorption phase, including the time to fill and empty the purge vessel 40, lasts about six minutes, the drying phase lasts about three minutes, and the desorbing and GC analysis phase lasts about five minutes. In general, automated system 100 is capable of handling about ten test samples per hour, which entails about 1.5 hours of test sample preparation for a forty-eight test sample batch.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto. For example, while the disclosed systems and methods have been described in detail in connection with the separation, detection and measurement of organomercury species, those of skill in the art will appreciate that the disclosed systems and methods may be effectively employed in the separation, detection and measurement of other chemical compounds and contaminants.

All of the publications, patent applications, and patents cited in this application are herein incorporated by reference in their entirety to the same extent as if each individual publication, patent application or patent was specifically and individually indicated to be incorporated by reference in its entirety.

The embodiments of the invention in which an exclusive property or privilege is claimed are defined as follows:

1. An automated system for processing a liquid test sample, comprising:
   (a) a gas and liquid separator configured for removing at least one volatile component from the test sample;
   (b) a first trapping vessel in fluid communication with the gas and liquid separator, wherein the first trapping vessel contains a trapping material capable of adsorbing at least one of the at least one volatile component to provide at least one adsorbed component; and
   (c) an infrared heat source configured for providing infrared emissions to heat the trapping material at the same location as adsorption to a temperature sufficient to release at least one of the at least one adsorbed component from the trapping material to provide at least one released component.

2. The system of claim 1, further comprising a sample container in fluid communication with the gas and liquid separator.

3. The system of claim 2, wherein the sample container is a hermetically sealable container.

4. The system of claim 2, further comprising a first conduit for delivering a first flow of gas to the sample container.

5. The system of claim 4, further comprising a purifier to purify the first flow of gas delivered to the sample container.

6. The system of claim 4, wherein the trapping vessel further includes an inlet configured to deliver a second flow of gas to remove the at least one released component from the trapping vessel.

7. The system of claim 2, further comprising a piercing needle assembly including at least one needle for piercing the sample container and transferring the test sample from the sample container to the gas and liquid separator.

8. The system of claim 1, wherein the test sample includes a metal compound.

9. The system of claim 1, wherein the test sample includes an organomercury compound.

10. The system of claim 9, wherein the organomercury compound is converted into at least one ethylated or propylated mercury species prior to entering the gas and liquid separator.

11. The system of claim 9, wherein the organomercury compound is a methyl mercury compound.

12. The system of claim 1, further comprising a gas chromatography column in fluid communication with the trapping vessel, the as chromatography column configured to separate at least two released components to provide at least two separated components.

13. The system of claim 12, further comprising a pyrolytic column in fluid communication with the gas chromatography column, wherein the pyrolytic column converts at least one separated component into elemental form.

14. The system of claim 13, further comprising a spectrophotometer for determining the amount of the elemental form.

15. The system of claim 1, wherein the infrared heat source is a halogen bulb.

16. The system of claim 1, wherein the infrared heat source is capable of heating the trapping material to a temperature of at least 150° C. in less than 25 seconds.

17. The system of claim 1, further including a second trapping vessel in fluid communication with the gas and liquid separator.

18. The system of claim 17, further including a third trapping vessel in fluid communication with the gas and liquid separator.

19. The system of claim 1, wherein the gas and liquid separator and the trapping vessel are in fluid communication by a plurality of tubular conduits formed from a fluoropolymer.

20. An automated system for processing a liquid test sample, comprising:
   (a) a gas and liquid separator configured for removing at least one volatile component from the test sample, wherein the at least one volatile component is selected from the group consisting of ethylated and propylated mercury species;
   (b) at least three trapping vessels in fluid communication with the gas and liquid separator, wherein the at least three trapping vessels contain a trapping material capable of adsorbing at least one volatile component to provide at least one adsorbed component, wherein the trapping material is in granular form, and wherein the three trapping vessels operate continuously such that during operation one trapping vessel is in an adsorbing phase, one trapping vessel is in a desorbing phase, and one trapping vessel is in a drying phase; and
   (c) an infrared heat source configured to heat the trapping material to a temperature sufficient to release at least one of the at least one adsorbed component from the trapping material to provide at least one released component.

21. An automated system for processing a liquid test sample, comprising:
   (a) a test sample container configured to contain a test sample and a reagent;
   (b) a first conduit for providing a flow of gas to the test sample container;
   (c) a gas and liquid separator in fluid communication with the first conduit, the gas and liquid separator configured for processing the entire test sample and removing at least one volatile component from the test sample using the flow of gas;
   (d) a trapping vessel in fluid communication with the gas and liquid separator, wherein the first trapping vessel contains a trapping material capable of adsorbing at least one of the at least one volatile component to provide at least one adsorbed component; and
   (e) an infrared heat source configured to heat the trapping material to a temperature sufficient to release at least one of the at least one adsorbed component from the trapping material to provide at least one released component.

22. An automated system for processing a liquid test sample, comprising:
   a) a gas and liquid separator;
   (b) an attachment for a first gas source that provides a flow of gas for removing at least one volatile component from the test sample in the gas and liquid separator, wherein an organomercury compound present in the test sample is converted to at least one ethylated or propylated mercury species prior to transfer of the test sample into the gas and liquid separator;

(c) a trapping vessel in fluid communication with the gas and liquid separator, wherein the trapping vessel contains at least one material capable of adsorbing the at least one ethylated or propylated mercury species of the organomercury compound, wherein the trapping material is in granular form; and (d) an infrared heat source providing infrared emissions for heating the at least one material in the trapping vessel at the same location as adsorption to a temperature sufficient to release the at least one ethylated or propylated mercury species from the at least one material.

23. A method for processing a liquid test sample, comprising:

(a) placing a liquid test sample and a reagent in a sealable container;

(b) transferring the entire sample from the container to a gas and liquid separator using a continuous first flow of gas;

(c) separating at least one volatile component from the sample in the gas and liquid separator using the first flow of gas;

(d) adsorbing at least one of the at least one volatile component onto a trapping material to provide at least one adsorbed component; and (e) releasing at least one of the at least one adsorbed component from the trapping material to provide at least one released component.

24. A method for processing a liquid test sample, comprising:

(a) placing a liquid test sample in a sealable container;

(b) transferring the sample from the container to a gas and liquid separator;

(c) separating at least one volatile component from the sample in the gas and liquid separator, wherein the at least one volatile component is selected from the group consisting of ethylated and propylated mercury species;

(d) adsorbing at least one of the at least one volatile component onto a trapping material to provide at least one adsorbed component, wherein the trapping material is in granular form; and (e) heating the trapping material by providing infrared emissions to a temperature sufficient to release at least one of the at least one adsorbed component from the trapping material to provide at least one released component.

25. A method for processing a liquid test sample, comprising:

(a) placing a liquid test sample in a sealable container;

(b) transferring the sample from the container to a gas and liquid separator;

(c) separating at least one volatile component from the sample in the gas and liquid separator, wherein the volatile component is selected from the group consisting of ethylated and propylated mercury species;

(d) adsorbing at least one of the at least one volatile component onto a trapping material in one of at least three trapping vessels in fluid communication with the gas and liquid separator to provide at least one adsorbed component, wherein the trapping material is in granular form, and wherein the three trapping vessels operate continuously such that during operation one trapping vessel is in an adsorbing phase, one trapping vessel is in a desorbing phase, and one trapping vessel is in a drying phase; and (e) releasing at least one of the at least one adsorbed component from the trapping material to provide at least one released component by heating the trapping material using an infrared heat source to a predetermined temperature.

* * * * *

UNITED STATES PATENT AND TRADEMARK OFFICE
CERTIFICATE OF CORRECTION

| | | |
|---|---|---|
| PATENT NO. | : 8,408,044 B2 | Page 1 of 1 |
| APPLICATION NO. | : 12/494200 | |
| DATED | : April 2, 2013 | |
| INVENTOR(S) | : P. Danilchik | |

It is certified that error appears in the above-identified patent and that said Letters Patent is hereby corrected as shown below:

In the Claims

COLUMN   LINE

15   61   "as chromatography" should read --gas chromatography--
(Claim 12, line 3)

Signed and Sealed this
Nineteenth Day of August, 2014

Michelle K. Lee
*Deputy Director of the United States Patent and Trademark Office*